United States Patent [19] [11] 4,384,994
Veber et al. [45] May 24, 1983

[54] RENIN INHIBITORY PEPTIDES

[75] Inventors: Daniel F. Veber, Ambler, Pa.; Daniel H. Rich, Madison, Wis.

[73] Assignee: Merck & Co., Inc., Rahway, N.J.

[21] Appl. No.: 309,854

[22] Filed: Oct. 8, 1981

[51] Int. Cl.$^3$ ................. C07C 103/52; A61K 37/02
[52] U.S. Cl. ........................... 260/112.5 R; 424/177
[58] Field of Search ................. 424/177; 260/112.5 R

[56] References Cited

U.S. PATENT DOCUMENTS

| | | | |
|---|---|---|---|
| 3,784,686 | 1/1974 | Miller | 424/94 |
| 3,873,681 | 3/1975 | Miller | 424/94 |
| 4,185,096 | 1/1980 | Castano et al. | 424/177 |
| 4,269,827 | 5/1981 | Burton et al. | 424/177 |

OTHER PUBLICATIONS

Sankyo K. K., "Japanese Patent Abstract", 2151–2166, Jun. 8, '76.
Umezawa, et al., J. Antibiot. (Tokyo) 23: 259–262, 1970.
Gross, et al., Science 175: 656, 1971.
Kokubu, et al., Biochem. Pharmacol. 22: 3217–3223, 1973.
Burton, et al., Biochemistry 14: 3892–3898, 1975.
Poulsen, et al., Biochemistry 12: 3877–3882, 1973.
Haber & Burton, Fed. Proc. Fed. Am. Soc. Exp. Biol. 38: 2768–2773, 1979.
Marshall Federation Proc. 35: 2494–2501, 1976.
Burton, et al., Proc. Natl. Acad. Sci. USA, 77: 5476–5479, 1980.
Suketa, et al., Biochemistry 14: 3188, 1975.
Swales, Pharmac. Ther. 7: 173–201, 1979.
Kokubu et al., Nature 217: 456–457, 1968.
Matsuchita, et al., J. Antibiotics 28: 1016–1018, Dec. 1975.
Lazar et al., Biochem. Pharma. 23: 2776–2778, 1974.
Miller et al., Biochem. Pharma. 21: 2941–2944, 1972.
Rich, et al., J. Org. Chem. 43: 3624, 1978.
J. Med. Chem. 23: 27, 1980.

Primary Examiner—Delbert R. Phillips
Assistant Examiner—F. T. Moezie
Attorney, Agent, or Firm—Raymond M. Speer; Hesna J. Pfeiffer

[57] ABSTRACT

Renin inhibitory peptides of the formula:

$$\text{Leu—Stav—Val—Phe} \qquad (I.)$$

and analogs thereof inhibit renin and are useful for treating various forms of renin-associated hypertension and hyperaldosteronism.

16 Claims, No Drawings

RENIN INHIBITORY PEPTIDES

BACKGROUND OF THE INVENTION

1. Field of the Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_i$):

| Class | $K_i$ (M) |
|---|---|
| Renin antibody | probably $10^{-6}$ |
| Pepstatin | $10^{-6} - 10^{-7}$ |
| Phospholipids | $10^{-3}$ |
| Substrate analogs | |
| Tetrapeptides | $10^{-3}$ |
| Octa- to tridecapeptides | $10^{-5} - 10^{-6}$ |

Umezawa et al., in J. Antibiot. (Tokyo) 23: 259–262, 1970, reported the isolation of a peptide from actinomyces that was an inhibitor of aspartyl proteases such as pepsin, cathepsin D, and renin. This peptide, known as pepstatin, was found by Gross et al., Science 175:656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

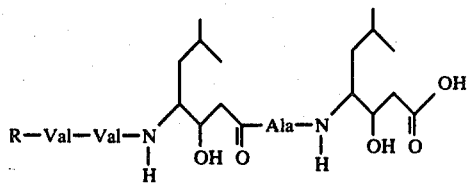

To date, many efforts have been made to prepare a specific renin inhibitor based on substrate analogy. It has been found, for example, that the octapeptide sequence extending from histidine-6 through tyrosine-13 has kinetic parameters essentially the same as those of the full tetradecapeptide renin substrate. The amino acid sequence of the octapeptide is as follows:

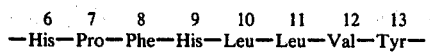

Renin cleaves this substrate between $Leu^{10}$ and $Leu^{11}$.

Kokubu et al., Biochem. Pharmacol. 22: 3217–3223, 1973, synthesized a number of analogs of the tetrapeptide found between residues 10 to 13, but while inhibition could be shown, inhibitory constants were only of the order of $10^{-3}$ M.

Analogs of a larger segment of renin substrate were also synthesized: Burton et al., Biochemistry 14: 3892–3898, 1975, and Poulsen et al., Biochemistry 12: 3877–3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, Fed. Proc. Fed. Am. Soc. Exp. Biol. 38: 2768–2773, 1979.

For other articles describing previous efforts to devise renin inhibitors, see Marshall, Federation Proc. 35: 2494–2501, 1976; Burton et al., Proc. Natl. Acad. Sci. USA 77: 5476–5479, Sept. 1980; Suketa et al., Biochemistry 14: 3188, 1975; Swales, Pharmac. Ther. 7: 173–201, 1979; Kokubu et al., Nature 217: 456–457, Feb. 3, 1968; Matsushita et al., J. Antibiotics 28: 1016–1018, Dec. 1975; Lazar et al., Biochem. Pharma. 23: 2776–2778, 1974; Miller et al., Biohem. Pharma. 21: 2941–2944, 1972; and Rich et al., J. Org. Chem. 43: 3624, 1978, and J. Med. Chem. 23: 27, 1980.

DETAILED DESCRIPTION OF THE INVENTION AND PREFERRED EMBODIMENTS

In accordance with the present invention there are provided renin inhibitory peptides of the formula:

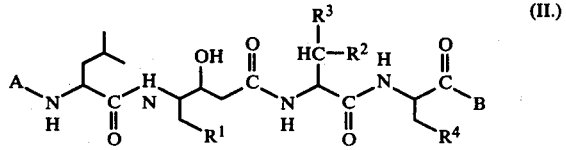

wherein:
A is hydrogen; or phenoxyacetyl;
R$^1$ is C$_{3-6}$ straight or branched alkyl; C$_{3-7}$ cycloalkyl; phenyl; or phenyl mono-substituted with hydroxyl, fluoro, chloro, bromo, methyl, or trifluoromethyl;
R$^2$ is hydrogen; or methyl;
R$^3$ is methyl; or isopropyl;
R$^4$ is phenyl; or 4-hydroxyphenyl; and
B is OR; NHR; or NR$_2$, where each R may be the same or different and is hydrogen or C$_{1-4}$ alkyl;
and a pharmaceutically acceptable salt thereof; all of the asymmetric carbon atoms having an S configuration.

The inhibitory peptides of the present invention may be shown as the following tetrapeptide or analogs thereof:

Leu-Sta-Val-Phe (I.)

in which a phenoxyacetyl group may be attached to the N-terminal of the tetrapeptide; statine may have additional alkyl or phenyl substitutions at the delta-position; valine may be leucine, phenylalanine may be tyrosine; and the C-terminal of the tetrapeptide may be the acid; or an ester or amide thereof. Thus, the inhibitory peptides of the present invention are essentially tetrapeptide substrate analogs.

Preferred peptides of the present invention are:
N-phenoxyacetyl-L-leucyl-(3S,4S)-statyl-L-valyl-L-phenylalanine;
N-phenoxyacetyl-L-leucyl-(3S,4S)-statyl-L-leucyl-L-phenylalanine;
N-phenoxyacetyl-L-leucyl-4(S)-amino-3(S)-hydroxy-5-phenylpentanoyl-L-leucyl-L-phenylalanine;
L-leucyl-(3S,4S)-statyl-L-valyl-L-phenylalanine;
L-leucyl-(3S,4S)-statyl-L-leucyl-L-phenylalanine;
L-leucyl-4(S)-amino-3(S)-hydroxy-5-phenylpentanoyl-L-leucyl-L-phenylalanine; and the amide and C$_{1-4}$ alkyl ester forms of the above peptides.

A particular feature of the present invention is the presence of the unusual amino acid, statine (Sta), which may be represented by the following formula:

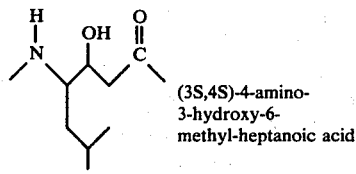

(3S,4S)-4-amino-3-hydroxy-6-methyl-heptanoic acid

The position of the statine is considered essential, since it has been found that the sequence:

Sta-Leu-Val-Phe has considerably less renin inhibitory potency than the novel peptides of the present invention.

Also within the scope of the present invention are modifications of the statine segment in accordance with the hydrophobicity required to maintain the inhibitory activity of the total peptide. Thus, the delta-position isopropyl substituent may be replaced with higher alkyl groups, cycloalkyl groups, phenyl, or substituted phenyl groups, as described above. The substitution of a phenyl group at this position is especially preferred.

It has also been found that, surprisingly, a phenoxyacetyl group attached to the N-terminal of the tetrapeptide dramatically increases the renin inhibitory potency.

The Formula II compounds can be used in the form of salts derived from inorganic or organic acids. Included among such salts are the following:
acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel peptides of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Renin-associated hypertension and hyperaldosteronism are effectively treated by the administration of from 96 milligrams to 7.2 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

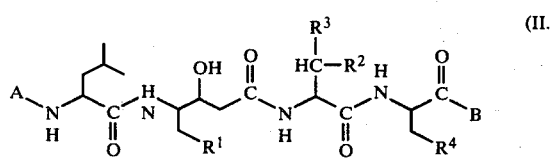

wherein:

A is hydrogen; or phenoxyacetyl;

$R^1$ is $C_{3-6}$ straight or branched alkyl; $C_{3-7}$ cycloalkyl; phenyl; or phenyl mono-substituted with hydroxyl, fluoro, chloro, bromo, methyl, or trifluoromethyl;

$R^2$ is hydrogen; or methyl;

$R^3$ is methyl; or isopropyl;

$R^4$ is phenyl; or 4-hydroxyphenyl; and

B is OR; NHR; or $NR_2$, where each R may be the same or different and is hydrogen or $C_{1-4}$ alkyl;

and a pharmaceutically acceptable salt thereof; all of the asymmetric carbon atoms having an S configuration.

Also, in accordance with the present invention there is still further provided a method of treating renin-associated hypertension and hyperaldosteronism, comprising administering to a patient in need of such treatment, a therapeutically effective amount of a peptide of the formula:

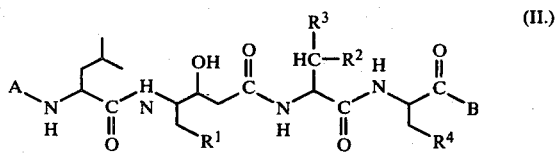

wherein:

A is hydrogen; or phenoxyacetyl;

$R^1$ is $C_{3-6}$ straight or branched alkyl; $C_{3-7}$ cyaloalkyl; phenyl; or phenyl mono-substituted with hydroxyl, fluoro, chloro, bromo, methyl, or trifluoromethyl;

$R^2$ is hydrogen; or methyl;

$R^3$ is methyl; or isopropyl;

$R^4$ is phenyl; or 4-hydroxyphenyl; and

B is OR; NHR; or $NR_2$, where each R may be the same or different and is hydrogen or $C_{1-4}$ alkyl;

and a pharmaceutically acceptable salt thereof; all of the asymmetric carbon atoms having an S configuration.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 1 to 10 mg per kg of body weight.

Both in vivo and in vitro methods may be employed. In the in vivo method, a novel peptide of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids. The unusual amino acid, statine, may be prepared in accordance with the procedure described in Rich et. al., *J. Org. Chem.* 43: 3624 (1978).

The phenoxyacetyl substituent may be prepared by treating the tetrapeptide with phenoxyacetic anhydride.

The following examples will serve to illustrate preparation of preferred novel peptides of the present invention.

EXAMPLE 1

N-tert-Butyloxycarbonyl-L-leucyl-(3S,4S)-statyl-L-valyl-L-phenylalanine methyl ester A. L-Phenylalanyl methyl ester hydrochloride A suspension of 16.52 g (100 mmol) of L-phenylalanine in 200 ml of anhydrous methanol was cooled in a ice-salt bath. Thionyl chloride (23.8 g, 200 mmol) was added dropwise over a period of 30 minutes. After the addition was completed, cooling was stopped and the reaction mixture was stirred at 25° for 20 hours. After heating under reflux for 30 minutes, the solution was cooled and freed of solvent on a rotary evaporator under reduced pressure to yield 21.29 g (98%) of L-Phe-OMe·HCl. TLC: $R_f$ 0.87 (10% MeOH in $CHCl_3$, few drops of $NH_4OH$).

B. N-tert-Butyloxycarbonyl-L-valine.

Boc-ON (13.55 g, 55 mmol) was added portionwise to a mixture of L-valine (5.86 g, 50 mmol), triethylamine (7.59 g, 10.4 ml, 75 mmol), $H_2O$ (30 ml) and p-dioxane (30 ml). A clear solution (yellowish) was obtained after stirring the suspension at 25° for 1 hour. After stirring for 4 hours more, water (75 ml) and ethyl acetate (100 ml) were added. The aqueous layer was separated and washed with ethyl acetate (150 ml). The colorless aqueous phase was acidified to pH 3 with cold 1 N HCl. Boc-Val was extracted with ethyl acetate (3×75 ml). The combined extracts were washed with saturated NaCl and then dried (Na$_2$SO$_4$/MgSO$_4$). Solvent removal on a rotary evaporator under reduced pressure followed by drying under high vacuum gave a highly viscous oil: 10.51 g (96.8%).

C. N-tert-Butyloxycarbonyl-L-Valyl-L-phenylalanyl methyl ester

To a stirred suspension of PheOMeHCl (431 mg, 2 mmol) in 8 ml of methylene chloride was added 220 mg (2.2 mmol) triethylamine at 0°. After stirring for 5 minutes, Boc-Val (435 mg, 2 mmol) and HOBt (297 mg, 2.2 mmol) were added. DCC (413 mg, 2 mmol) in 2 ml of CH$_2$Cl$_2$ was then added to the reaction mixture. After stirring at 4° C. for 20 hours the reaction mixture was concentrated under reduced pressure. Ether (30 ml) was added and the mixture was chilled in an ice bath. The solids were then removed by suction filtration. Cooling and removal of any solids was repeated twice. The filtrate was then consecutively washed with saturated NaHCO$_3$, cold 1 N HCl, and saturated NaCl solution. After drying the ethereal layer (Na$_2$SO$_4$-MgSO$_4$) the solvent was removed on a rotary evaporator under reduced pressure to afford 597 mg (79% yield) of a white solid: TLC, R$_f$ 0.67 (5% MeOH/CHCl$_3$ HOAc) single spot. NMR (CDCl$_3$) δ 0.90, 0.96 (6H, d,d ratio 1:3, J=7.5 Hz, Val CH$_3$), 1.51 (9H, S, Boc), 2.13 (1H, bq, J-8 Hz, Val CH), 3.18 (2H, m, PheCH$_2$), 3.79 (3H, S, OCH$_3$), 3.98 (1H, m, ValαCH), 4.98 (1H, q, J-7.5 Hz, PheαCH), 5.13 (1H, bd, J=7.5 Hz, BocNH), 6.46 (1H, bs, NH), 7.24, 7.59 (5H, m, aromatic CH).

Anal. Calcd. for C$_{20}$H$_{30}$N$_2$O$_5$: C, 63.47; H, 7.99; N, 7.40. Found: C, 63.57; H, 8.08; N, 7.37.

D. L-Valyl-phenylalanyl methyl ester hydrochloride

Boc-Val-Phe-OMe (500 mg) was treated with 10 ml of anhydrous 4 N HCl in dioxane. The solution was then stirred at 25° for 30 minutes. Deprotection, followed by TLC, was complete. After removal of solvent the resulting oil was triturated with ether to form a precipitate which was collected by filtration. The solid was washed several times with ether and then dried under high vacuum to give 402 mg (97% yield) of the desired compound as a hygroscopic solid: [α]$_D^{24}$+27.94° (C=0.93 MeOH).

E. N-tert-Butyloxycarbonyl-(3S,4S)-statyl-L-valyl-L-phenylalanine methyl ester Triethylamine (250 mg, 2.47 mmol) was added to a stirred suspension of valyl-phenylalanine methyl ester hydrochloride (717 mg, 2.27 mmol) in 10 ml of CH$_2$Cl$_2$. The clear solution was cooled to 0° and the following were added in the order given: Boc-(S,S)-statine (564 mg, 2.05 mmol), HOBt (386 mg, 2.52 mmol), DCC (467 mg, 2.27 mmol) in 5 ml of CH$_2$Cl$_2$. After stirring at 5° for 10 hours the mixture was chilled on dry ice. The ppt of N,N'-dicyclohexyl urea was removed by vacuum filtration. The filtrate was again chilled on dry ice and N,N'-dicyclohexyl urea removed by filtration. The filtrate was washed with ice-cold 0.5 N NaOH, 1 N HCl and saturated NaCl. The methylene chloride solution was then dried (MgSO$_4$) and evaporated in vacuo to give a white solid (1.40 g). The crude product was purified on a column of silica gel (100 g,. 2.5 cm i.d.) eluting with 500 ml of CHCl$_3$ followed by 500 ml of 5% MeOH in CHCl$_3$. Fractions containing the desired tripeptide were combined and evaporated to give 1.00 g (90.6%) of the desired compound. TLC: R$_f$ 0.52 (10% MeOH/CHCl$_3$), R$_f$ 0.16 (5% MeOH/CHCl$_3$). [α]$_D^{24}$−51.37° (C=0.985, MeOH).

NMR (CDCl$_3$) δ 0.87-1.02 (12H, two d, J-10 Hz, Sta and Val-CH$_3$), 1.32-1.76 (13H, m; includes δ 1.47, S; δ 1.76, S, exchangeable), 2.13 (1H, bq, J=8 Hz, ValCH), 2.34-2.54 (2H, m, sta CH$_2$-C=O), 3.17 (2H, t, J≈5 Hz, PheCH$_2$), 3.67 (1H, m), 3.78 (3H, S, CO$_2$-CH$_3$), 4.02 (1H, bm, ValαCH), 4.13 (1H, d, J≈1 Hz, exchangeable), 4.31 (1H, bt, J≈8 Hz), 4.88 (1H, d, J=10 Hz, exchangeable), 4.96 (1H, q, J≈8 Hz, PheαCH), 6.64 (1H, d, J=10 Hz, NH), 6.70 (1H, d, J=10 Hz, NH), 7.23, 7.37 (5H, m, aromatic CH).

F. (3S, 4S) Statyl-L-valyl-L-phenylalanine methyl ester hydrochloride

Boc-(S,S)-Sta-Val-Phe-OMe (800 mg 1.5 mmol) was treated with 15 ml of anhydrous 4.5 N HCl/p. dioxane. After stirring for 45 minutes at 25°, analysis by TLC indicated that deprotection was complete. The residual oil obtained after removal of solvent was triturated with ether and the precipitate of the title compound was collected by vacuum filtration. Drying under high vacuum gave 701 mg (92.7%) of the desired compound as a white solid: [α]$_D^{24}$−21.21° (C=1.02, MeOH).

G. N-tert-Butyloxycarbonyl-L-leucyl-(3S,4S)statyl-L-valyl-L-phenylalanine methyl ester Triethylamine (120 mg, 1.2 mmol) was added to a stirred suspension of (3S,4S)statyl-L-valyl-L-phenylalanine methyl ester hydrochloride (566 mg, 1.2 mmol) in 10 ml of CH$_2$Cl$_2$ at 0°. Then HOBt (184 mg, 1.2 mmol) and Boc-leucine hydrate (300 mg, 1.2 mmol) were added. After 5 minutes, DCC (248 mg, 1.2 mmol) in 5 ml of CH$_2$Cl$_2$ was added to the reaction mixture. Stirring was continued at 5° for 23 hours after which TLC indicated the reaction was finished. The reaction mixture was cooled on dry ice and the precipitate of N,N'-dicyclohexyl urea removed by filtration. The cooling and filtration procedure was repeated twice. The filtrate was diluted with 25 ml of CH$_2$Cl$_2$ and washed with ice cold 0.5 N NaOH, 1 N HCl and brine. The organic layer was dried (MgSO$_4$) and concentrated in vacuo. The residual (white solid) was purified by chromatograph over silica gel (60 g, 2 cm i.d.) eluting with 500 ml CHCl$_3$ followed by 500 ml of 7% MeOH/CHCl$_3$ to afford 650 mg (83% yield) of the desired compound: TLC, single spot 0.53 (10% MeOH/CHCl$_3$). [α]$_D^{24}$−49.90 (C=1.0, McOH).

NMR (CDCl$_3$) δ 0.8-1.08 (18H, m), 1.3-2.75 (18H, includes δ 1.47, S), 3.09 (2H, d, J≈10 Hz), 3.47 (1H, bm), 3.67 (3H, S, OCH$_3$), 3.80-4.24 (3H, m), 4.75-5.28 (3H, m), 6.90 (1H, d, J=8 Hz, NH), 7.1-7.3 (5H, m, aromatic CH), 7.46 (1H, bd, J≈8 Hz, NH), 7.70 (1H, bd, J≈8 Hz, NH).

Mass spectrum M+ calcd. 648.3098. Found 648.4012. m/e (% relative intensity) 651(0.06), 650(0.41), 649(1.98), 648(4.29), 575(3.2), 442(4.1), 396(5.1), 386(5.7), 369(7.7), 368(25.5), 350(15.2), 349(27.9), 342(35.6), 300(35.9), 244(57.6), 180(65.7), 158(36.4), 140(31), 130(36.9), 120(41.4), 86(100), 72(86.9).

Anal. Calcd. for C$_{34}$H$_{56}$N$_4$O$_8$: C, 62.94; H, 8.70; N, 8.64. Found: C, 62.88; H, 8.71; N, 8.56.

EXAMPLE 2

N-Phenoxyacetyl-L-leucyl-(3S,4S)-statyl-L-valyl-L-phenylalanine methyl ester The hydrochloride salt obtained from the reaction of Boc-Leu-(3S, 4S)-Sta-Val-Phe-OMe (260 mg, 0.4 mmol) with 4 N HCl in dioxane (ca 8 ml) was dissolved in 8 ml of methylene chloride and 0.5 ml of dimethylformamide. Triethyl amine (0.056 ml, 0.4 mmol) and phenoxyacetic anhydride, (0.137 g, 0.49 mmol) were then added at 0° to this solution. The reaction mixture was stirred at 0°–4° for 20 hrs and at room temperature for 3 hrs. Ethyl acetate was added and the mixture was washed with cold 0.2 N NaOH, in HCl and brine. The organic phase was dried ($Na_2SO_4$) and evaporated to dryness. The crude product was purified by chromatography over silica gel eluting with a gradient of 0–5% methanol in chloroform to afford the title compound in about 70% yield.

Anal. Calcd. for $C_{37}H_{54}N_4O_8$: C, 65.08; H, 7.97; N, 8.21. Found: C, 65.17; H, 8.02; N, 8.19.

EXAMPLE 3

N-Phenoxyacetyl-L-leucyl-(3S, 4S)-statyl-L-leucyl-L-phenylalanine methyl ester A solution of Leu-3S,4S-Sta-Leu-Phe-OMe.HCl (48 mg, 0.08 mmol) in dimethylformamide (0.7 ml) was neutralized with N-methylmorpholine (8.1 µl, 0.08 mmol) and then treated with phenoxyacetic anhydride (34 mg, 0.12 mmol) at 4°. The reaction mixture was stirred at 0°–4° for 26 hrs. The solvent was removed under reduced pressure and the resulting residue was taken up in ethyl acetate. The ethyl acetate layer was then sequentially washed with ice cold 0.1 N NaOH, 1 N HCl, and brine. The organic layer was dried over anhydrous sodium sulfate and stripped of solvent in vacuo. The crude product was purified by preparative TLC on silica gel eluting with 8% methanol in chloroform to give the title compound in 73% yield.

TLC (solvent B); Rf 0.32; (solvent C) Rf 0.62. NMR 270 MHz (CDCl$_3$), δ 0.87–1.0 (m 18H, six CH$_3$), 1.44–1.85 (m, 9H), 2.20 (m, 1H), 2.68 (m, 1H), 3.13 (d, J=6 Hz, 2H, Pheβ), 3.42 (b, 1H), 3.66–3.83 (m, 4H, includes singlet at δ 3.73), 4.1 (m, 1H), 4.33 (m, 2H) 4.49–4.65 (m, 3H, includes doublet at δ 4.55, J=4.5 Hz), 4.94 (m, 1H), 6.62 (d, J=7.5 Hz, 1H, NH), 7.00 (d, J=8 Hz, 1H, NH), 7.21 (d, J=7.5 Hz, 1H), 7.29–7.48 (m, 10H, Ar), 7.92 (b, 1H, NH).

Anal. Calcd. for $C_{38}H_{56}N_4O_8$: C, 65.49; H, 8.10; N, 8.04. Found: C, 65.57; H, 8.19; N, 7.98.

EXAMPLE 4

N-Phenoxyacetyl-L-leucyl-4(S)-amino-3(S)-hydroxy-5-phenylpentanoyl-L-leucyl-L-phenylalanine methyl ester

A. N-tert-Butyloxycarbonyl-L-leucyl-L-phenylalanine methyl ester

Triethylamine (1.85 ml, 13.3 mmol) was added to a stirred suspension of phenylalanine methyl ester hydrochloride (2.87 g, 13.3 mmol), prepared as in Step A of Example 1, in 50 ml of methylene chloride. The resulting clear solution was cooled to 0° C. and the following were added: Boc-Leu-OH (3.32 g, 13.3 mmol), HOBt (3.05 g, 20 mmol), and DCC (2.74 g, 13.3 mmol). Reaction and work-up were carried out according to procedure B in Rich, J. Med. Chem., 23, 27(1980). The crude product was purified by chromatography over silica gel eluting with 2% methanol in chloroform to give 4.82 g (92%) of the desired protected dipeptide. $[α]_D^{23}$ −26.08 (c=1.09, methanol) TLC (D): $R_f$−0.61.

NMR(CDCl$_3$) & 0.91 (d,J=5.5 Hz, 6H, LeuCH$_3$), 1.19–1.85 (m, 12H, Leu β and, includes singlet at & 1.43 (Boc CH$_3$), 3.10 (d,J=5.6 Hz, 2H, Pheβ), 3.66 (S, 3H, OCH$_3$), 4.06 (bm, 1H, leuα), 4.64–5.00 (m, 2H, Pheα-BocNH), 6.45 (d,J=8 Hz, 1H, PheNH), 7.00–7.30 (m, 5H, aromatic).

Anal. Calcd. for $C_{21}H_{32}N_2O_5$: C, 64.26; H, 8.22; N, 7.14 Found: C, 64.49; H, 8.34; N, 7.20.

B. N-tert-Butyloxycarbonyl-4(S)-amino-3(S)-hydroxy-5-phenylpentanoyl-L-leucyl-L-phenylalanine methyl ester Following procedure A in Rich, J. Med. Chem., 23, 27 (1980), Boc-Leu-Phe-OMe(1.07 g, 2.73 mmol) was treated with 4NHCl in dioxane (ca 25 ml). The resulting hydrochloride was dissolved in ca 3 ml of dimethylformamide and 30 ml of methylene chloride and allowed to react with N-methylmorpholine (0.3 ml, 2.73 mmol), Boc-4(S)-amino-3(S)-hydroxy-5-phenylpentanoic acid or (3S,4S)-AHPPA, prepared as described in Rich, J. Med. Chem., 23, 27 (1980) (0.806 g, 2.73 mmol), HOBt(0.626 g, 4.09 mmol), and DCC (0.562 g, 2.73 mmol) according to procedure B. The crude product (2.2 g) was purified by chromatography over silica gel eluting with 1% methanol in chloroform to give 1.2 g (75% yield) of the desired protected tripeptide.

NMR (CDCl$_3$) δ 0.77–0.95(bm, 6H), 1.30–1.78 (m, 12H, includes Boc singlet at δ 1.40), 2.00–2.66 (m, 2H, AHPPA, 2.80–3.20(4H, benzyl), 3.60–3.75) (m, 4H, AHPPA, includes methyl ester singlet at δ 3.70), 3.90 (m, 1H, AHPPA-C$_3$), 4.20–4.49 (m, 2H, Leu γH, OH), 4.70–5.00 (m, 2H, Pheα, Boc NH), 6.20(d,J=8 Hz, 1H, NH), 6.51 (d, J=7.5 Hz, 1H, NH), 7.00–7.50 (m, 10H, aromatic H).

Anal. Calcd. for $C_{32}H_{45}N_3O_7$: C, 65.84; H, 7.77; N, 7.19. Found: C, 65.65; H, 7.74; N, 7.05.

C. N-tert-Butyloxycarbonyl-L-leucyl-4(S)-amino-3(S)-hydroxy-5-phenylpentanoyl-L-leucyl-L-phenylalanine methyl ester Following procedure A in Rich, J. Med. Chem. 23, 27 (1980), Boc (3S,4S)-AHPPA-Leu-Phe-OMe (0.7 g, 1.2 mmol), was treated with ca 10 ml of 4NHCl in dioxane. The solvent was removed in vacuo at 25° C. and the residue was dried under high vacuum for 5 hours. (3S,4S)-AHPPA-Leu-Phe-OMe HCl thus obtained was dissolved in ca 15 ml of methylene chloride and treated with N-methylmorpholine (0.132 ml, 1.2 mmol) Boc-Leu-(0.278 g, 1.2 mmol), HOBt(0.27 g, 1.8 mmol) and DCC(0.25 g, 1.2 mmol), according to procedure B. The crude product was purified by chromatography over silica gel eluting with a gradient of 0–5% methanol in chloroform to give the title compound in 87% yield.

NMR (CDCl$_3$) δ 0.71–0.92(m, 12H), 1.26–1.87(m, 15H, include Boc singlet at δ 1.45) 2.0–2.33(m, 1H, AHPPA C$_2$) 2.60–2.93(m, 1H, AHPPA C$_2$), 3.02–3.19 (m, 4H, benzyl), 3.46–3.67(m, 4H, AHPPA C$_4$, and methyl ester singlet at δ 3.61), 3.77(m, 1H, AHPHA C$_3$), 4.03–4.51(m, 2H), 4.68–5.00(m, 2H, one exchangeable), 5.42 (d, J=10 Hz, 1H exchangeable) 6.50(d, J=8 Hz, 1H, NH), 7.16–7.30(m, 10H, aromatic), 7.24(d, J=7.5 Hz, NH), 7.47(d, J=7 Hz, 1H NH). In addition to these the following minor resonances were observed for NHs at δ 6.07(m), 6.88(d, J=9 Hz), 8.37(d, J=7.5H)-(probably arising from different conformations).

Anal. Calcd. for $C_{38}H_{56}N_4O_8$: C, 65.49; H, 8.10; N, 8.04. Found: C, 65.39; H, 8.09; N, 7.96.

D. N-Phenoxyacetyl-L-leucyl-4(S) amino-3(S)hydroxy-5-phenylpentanoyl-L-leucyl-L-phenylalanine methyl ester Boc-Leu-(3S,4S)-AHPPA-Leu-Phe-OMe (0.237 mg, 0.34 mmol) was allowed to react with 4NHCl in dioxane (ca 5 ml) according to procedure A in Rich, J. Med. Chem., 23, 27 (1980). The resulting hydrochloride was dissolved in ca 5 ml of methylene chloride and neutralized with N-methylmorpholine (0.037 ml, 0.34 mmol). The reaction mixture was cooled to 0° C. and phenoxyacetic anhydride (0.146 g, 0.51 mmol) was added. The mixture was stirred at 0°-4° C. for 18 hours and then at room temperature for 2 hours. Ethyl acetate was added to the reaction mixture and the solution was washed with cold 0.2 N NaOH, in HCl and brine. The organic layer was dried ($Na_2SO_4$ and evaporated to dryness. Trace impurities from the crude product were removed by chromatography over silica gel eluting with 1% methanol in chloroform to afford the title compound in 82% yield. NMR ($CDCl_3$) δ 0.75-0.92 (m, 12H Leu methyls), 1.28-1.76 (m, 6H, Leu β and γ), 2.05-2.35 (m, 1H, AHPPA $C_2$), 2.51-2.93 (m, 1H, AHPPA $C_2$), 3.02-3.20 (m, 4H, φ benzyl), 3.49-3.83 (m, 4H, AHPPA $C_4$) and includes methyl ester singlet at δ 3.62), 4.01-4.40 (m, 5H, AHPPA $C_3$, 2 Leuα includes singlet at δ 4.49 φ-O-CH), 4.66-4.92 (m, 1H, Phe α), 5.15 (d, J=10 Hz, 1H, exchangeable OH), 6.58 (d, J=8 Hz, 1H, NH), 6.71-7.46 (m, 17H, 2 NH, 15 aromatic), 7.86 (d, J=7 Hz, 1H, NH).

What is claimed is:
1. A peptide of the formula:

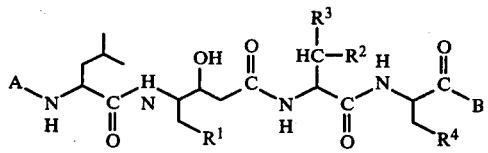

(II.)

wherein:
A is hydrogen; or phenoxyacetyl;
$R^1$ is $C_{3-6}$ straight or branched alkyl; $C_{3-7}$ cycloalkyl; phenyl; or phenyl monosubstituted with hydroxyl, fluoro, chloro, bromo, methyl, or trifluoromethyl;
$R^2$ is hydrogen; or methyl;
$R^3$ is methyl; or isopropyl;
$R^4$ is phenyl; or 4-hydroxyphenyl; and
B is OR; NHR; or $NR_2$, where each R may be the same or different and is hydrogen or $C_{1-4}$ alkyl;
and a pharmaceutically acceptable salt thereof; all of the asymmetric carbon atoms having an S configuration.

2. A peptide according to claim 1 wherein the peptide is N-phenoxyacetyl-L-leucyl-(3S,4S)-statyl-L-valyl-L-phenylalanine, or the amide or $C_{1-4}$alkyl ester form thereof.

3. A peptide according to claim 1 wherein the peptide is N-phenoxyacetyl-L-leucyl-(3S,4S)-statyl-L-leucyl-L-phenylalanine, or the amide or $C_{1-4}$alkyl ester form thereof.

4. A peptide according to claim 1 wherein the peptide is N-phenoxyacetyl-L-leucyl-4(S)-amino-3(S)-hydroxy-5-phenylpentanoyl-L-leucyl-L-phenylalanine, or the amide or $C_{1-4}$alkyl ester form thereof.

5. A peptide according to claim 1 wherein the peptide is L-leucyl-(3S,4S)-statyl-L-valyl-L-phenylalanine, or the amide or $C_{1-4}$alkyl ester form thereof.

6. A peptide according to claim 1 wherein the peptide is L-leucyl-(3S,4S)-statyl-L-leucyl-L-phenylalanine, or the amide or $C_{1-4}$alkyl ester form thereof.

7. A peptide according to claim 1 wherein the peptide is L-leucyl-4(S)-amino-3(S)-hydroxy-5-phenylpentanoyl-L-leucyl-L-phenylalanine, or the amide or $C_{1-4}$alkyl ester form thereof.

8. A pharmaceutical composition for treating renin-associated hypertension, comprising a pharmaceutical carrier and a therapeutically effective amount of a peptide of the formula:

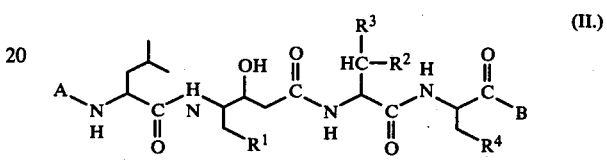

(II.)

wherein:
A is hydrogen; or phenoxyacetyl;
$R^1$ is $C_{3-6}$ straight or branched alkyl; $C_{3-7}$ cycloalkyl; phenyl; or phenyl monosubstituted with hydroxyl, fluoro, chloro, bromo, methyl, or trifluoromethyl;
$R^2$ is hydrogen; or methyl;
$R^3$ is methyl; or isopropyl;
$R^4$ is phenyl; or 4-hydroxyphenyl; and
B is OR; NHR; or $NR_2$, where each R may be the same or different and is hydrogen or $C_{1-4}$ alkyl;
and a pharmaceutically acceptable salt thereof; all of the asymmetric carbon atoms having an S configuration.

9. A pharmaceutical composition according to claim 8 wherein the peptide is N-phenoxyacetyl-L-leucyl-4(S)-amino-3(S)-hydroxy-5-phenylpentanoyl-L-leucyl-L-phenylalanine, or the amide or $C_{1-4}$alkyl ester form thereof.

10. A method of treating renin-associated hypertension comprising administering to a patient in need of such treatment, a therapeutically effective amount of a peptide of the formula:

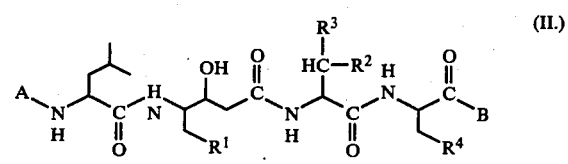

(II.)

wherein:
A is hydrogen; or phenoxyacetyl;
$R^1$ is $C_{3-6}$ straight or branched alkyl; $C_{3-7}$ cycloalkyl; phenyl; or phenyl monosubstituted with hydroxyl, fluoro, chloro, bromo, methyl, or trifluoromethyl;
$R^2$ is hydrogen; or methyl;
$R^3$ is methyl; or isopropyl;
$R^4$ is phenyl; or 4-hydroxyphenyl; and
B is OR; NHR; or $NR_2$, where each R may be the same or different and is hydrogen or $C_{1-4}$ alkyl;
and a pharmaceutically acceptable salt thereof; all of the asymmetric carbon atoms having an S configuration.

11. A method according to claim 10 wherein the peptide is N-phenoxyacetyl-L-leucyl-4(S)-amino-3(S)- hydroxy-5-phenylpentanoyl-L-leucyl-L-phenylalanine, or the amide or C$_{1-4}$alkyl ester form thereof.

12. A pharmaceutical composition for treating renin-associated hyperaldosteronism, comprising a pharmaceutical carrier and a therapeutically effective amount of a peptide of the formula:

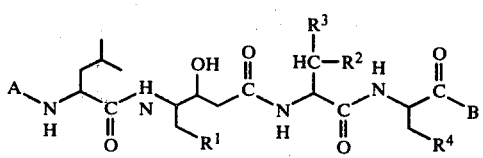
(II.)

wherein:

A is hydrogen; or phenoxyacetyl;

R$^1$ is C$_{3-6}$ straight or branched alkyl; C$_{3-7}$ cycloalkyl; phenyl; or phenyl monosubstituted with hydroxyl, fluoro, chloro, bromo, methyl, or trifluoromethyl;

R$^2$ is hydrogen; or methyl;

R$^3$ is methyl; or isopropyl;

R$^4$ is phenyl; or 4-hydroxyphenyl; and

B is OR; NHR; or NR$_2$, where each R may be the same or different and is hydrogen or C$_{1-4}$ alkyl;

and a pharmaceutically acceptable salt thereof; all of the asymmetric carbon atoms having an S configuration.

13. A pharmaceutical composition according to claim 12 wherein the peptide is N-phenoxyacetyl-L-leucyl-4(S)-amino-3(S)-hydroxy-5-phenylpentanoyl-L-leucyl-L-phenylalanine, or the amide or C$_{1-4}$alkyl ester form thereof.

14. A method of treating renin-associated hyperaldosteronism, comprising administering to a patient in need of such treatment, a therapeutically effective amount of a peptide of the formula:

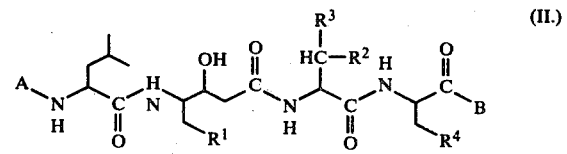
(II.)

wherein:

A is hydrogen; or phenoxyacetyl;

R$^1$ is C$_{3-6}$ straight or branched alkyl; C$_{3-7}$ cycloalkyl; phenyl; or phenyl monosubstituted with hydroxyl, fluoro, chloro, bromo, methyl, or trifluoromethyl;

R$^2$ is hydrogen; or methyl;

R$^3$ is methyl; or isopropyl;

R$^4$ is phenyl; or 4-hydroxyphenyl; and

B is OR; NHR; or NR$_2$, where each R may be the same or different and is hydrogen or C$_{1-4}$alkyl;

and a pharmaceutically acceptable salt thereof; all of the asymmetric carbon atoms having an S configuration.

15. A method according to claim 14 wherein the peptide is N-phenoxyacetyl-L-leucyl-4(S)-amino-3(S)-hydroxy-5-phenylpentanoyl-L-leucyl-L-phenylalanine, or the amide or C$_{1-4}$alkyl ester form thereof.

16. A method of determining the presence of renin-associated hypertension in a patient, comprising administering to such a patient, at a hypotensive dosage level and as a single dose, a peptide of the formula:

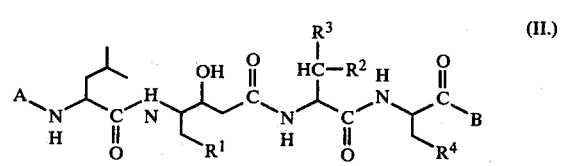
(II.)

wherein:

A is hydrogen; or phenoxyacetyl;

R$^1$ is C$_{3-6}$ straight or branched alkyl; C$_{3-7}$ cycloalkyl; phenyl; or phenyl monosubstituted with hydroxyl, fluoro, chloro, bromo, methyl, or trifluoromethyl;

R$^2$ is hydrogen; or methyl;

R$^3$ is methyl; or isopropyl;

R$^4$ is phenyl; or 4-hydroxyphenyl; and

B is OR; NHR; or NR$_2$, where each R may be the same or different and is hydrogen or C$_{1-4}$ alkyl;

and a pharmaceutically acceptable salt thereof; all of the asymmetric carbon atoms having an S configuration; followed by monitoring of said patient's blood pressure.

* * * * *